United States Patent [19]

Igari et al.

[11] Patent Number: 4,588,402
[45] Date of Patent: May 13, 1986

[54] CONNECTOR FOR MEDICAL TUBING AND MEDICAL SOLUTION BAG DEVICE USING THE CONNECTOR

[75] Inventors: Akira Igari, Tokyo; Keinosuke Isono, Kawaguchi, both of Japan

[73] Assignee: Terumo Kabushiki Kaisha, Tokyo, Japan

[21] Appl. No.: 729,080

[22] Filed: May 1, 1985

Related U.S. Application Data

[63] Continuation of Ser. No. 425,883, Sep. 28, 1982, abandoned.

[30] Foreign Application Priority Data

Mar. 9, 1982 [JP]  Japan .................................. 57-35722
Mar. 24, 1982 [JP] Japan .................................. 57-45673

[51] Int. Cl.⁴ ...................... A61B 19/00; A61M 25/00
[52] U.S. Cl. .................................. 604/408; 604/285; 604/905; 29/DIG. 35; 285/905
[58] Field of Search ............... 604/280, 283, 408, 905; 29/DIG. 35; 285/DIG. 6

[56] References Cited

U.S. PATENT DOCUMENTS

| | | | |
|---|---|---|---|
| 3,502,097 | 3/1970 | Muller | 604/280 |
| 4,206,537 | 6/1980 | Meginnis | 29/DIG. 35 |
| 4,270,534 | 6/1981 | Adams | 604/905 |
| 4,296,949 | 10/1981 | Mutterties et al. | 604/905 |
| 4,397,522 | 8/1983 | Parr | 285/DIG. 6 |
| 4,432,764 | 2/1984 | Lopez | 604/283 |
| 4,491,347 | 1/1985 | Gustafson | 285/DIG. 6 |

FOREIGN PATENT DOCUMENTS 1193759 6/1970 United Kingdom .
2024974 1/1980 United Kingdom .

OTHER PUBLICATIONS

USA Standard Dimensions of Glass and Metal Luer Tapers for Medical Applications (8/1955).

Primary Examiner—C. Fred Rosenbaum
Assistant Examiner—Michelle N. Lester
Attorney, Agent, or Firm—Frishauf, Holtz, Goodman & Woodward

[57] ABSTRACT

A connector for medical tubing for liquid transfusion includes a short tubular male connector member made of thermally resistant corrosionproof materia; a short tubular female connector member made of thermally resistant corrosionproof material; and a fitting surface portion on the outer surface of an insertion end of the male connector, shaped in the male form and made of a material having a smaller thermal expansion coefficient than the material of a corresponding fitting surface portion on the inner surface of an insertion end of the female connector shaped in the female form. The fitting surface portion of the insertion end shaped in the male form, and the fitting surface portion of the insertion end shaped in the female form, are of relative sizes such as to permit the insertion ends to be connected to and separated from each other by shrink fit utilizing the difference between the thermal expansion coefficients thereof. A medical solution bag device using the connector is also disclosed.

35 Claims, 14 Drawing Figures

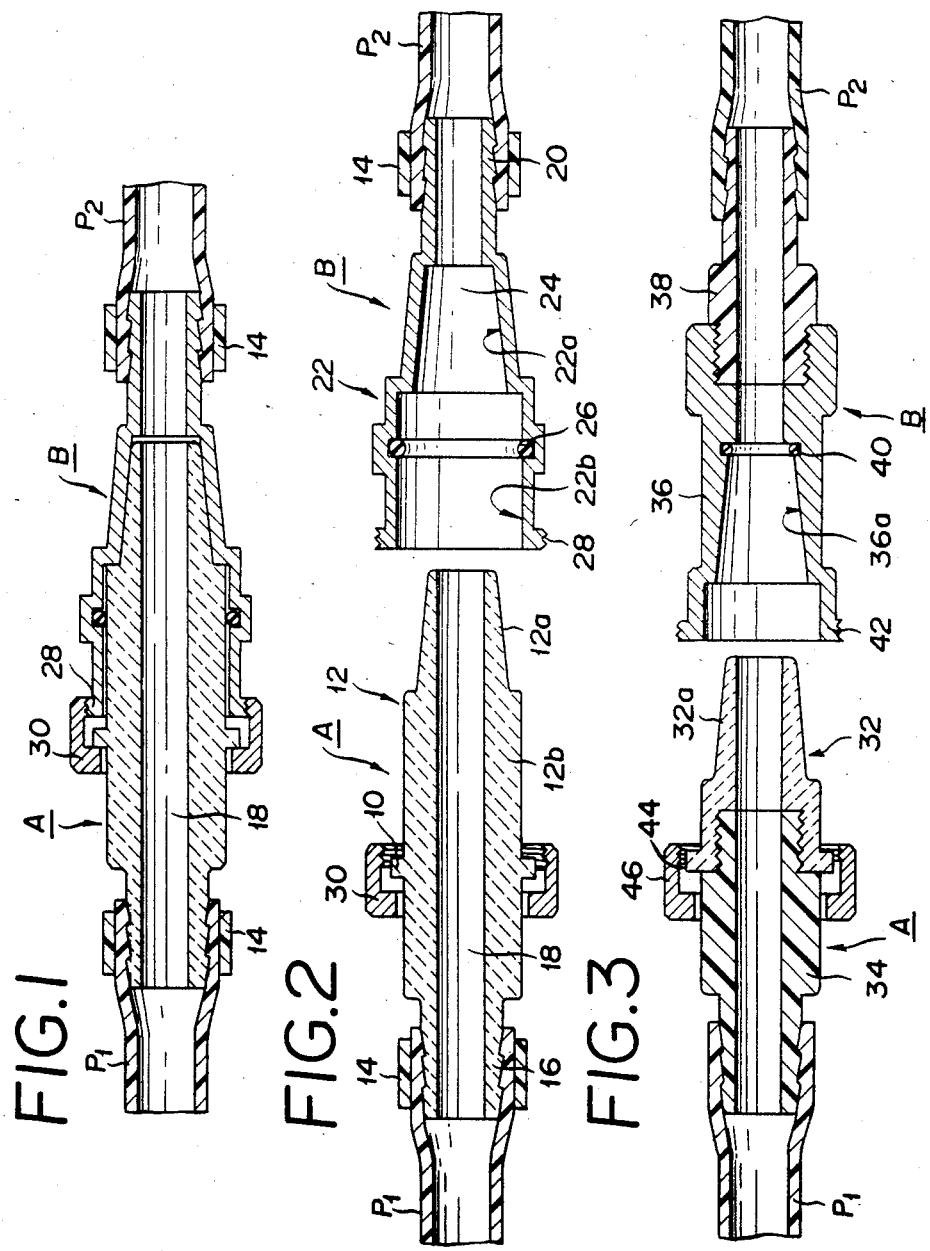

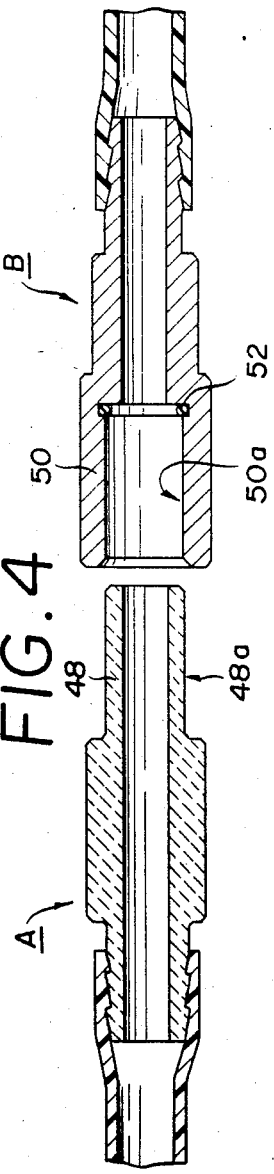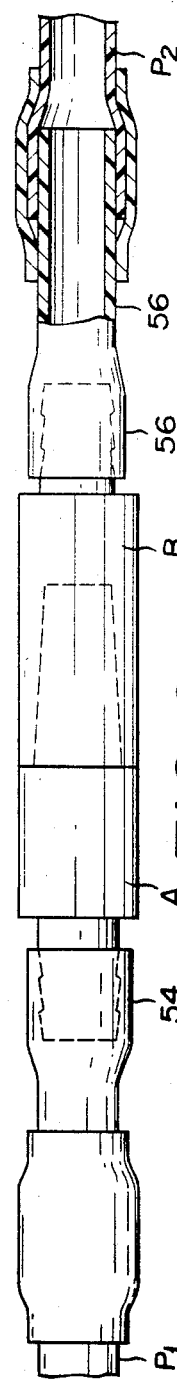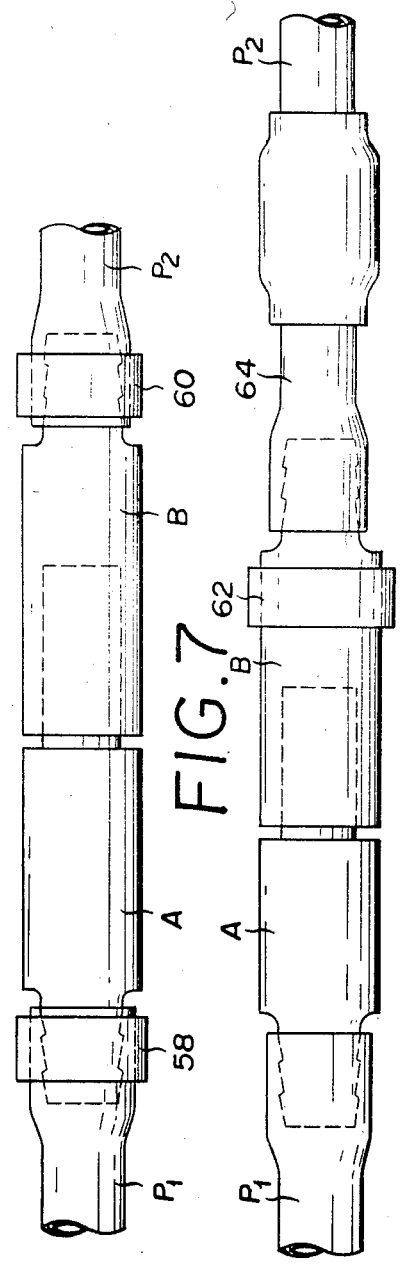

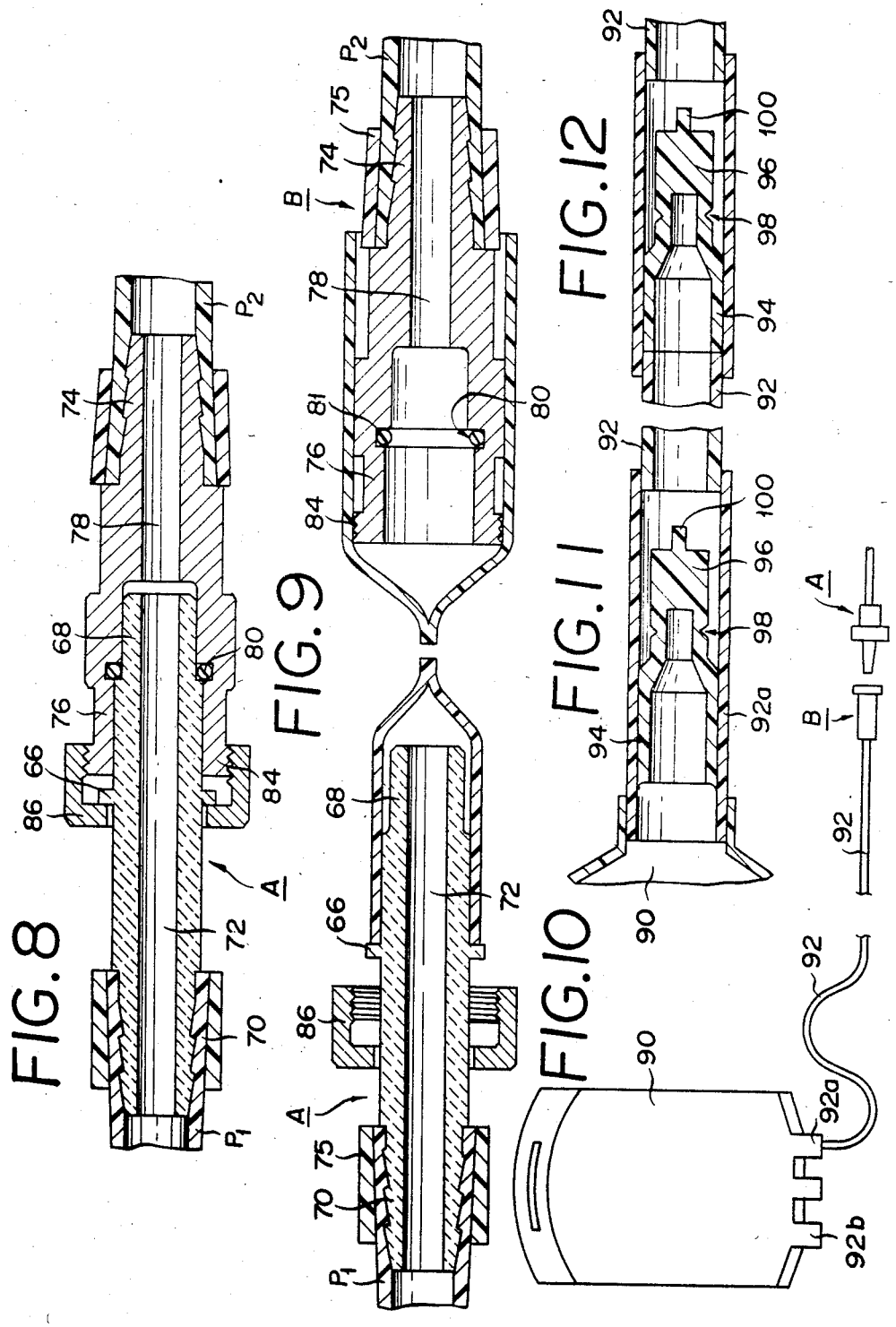

CONNECTOR FOR MEDICAL TUBING AND MEDICAL SOLUTION BAG DEVICE USING THE CONNECTOR

This application is a continuation of application Ser. No. 425,883, filed Sept. 18, 1982, abandoned.

BACKGROUND OF THE INVENTION

1. Field of the Invention

This invention relates to a connector for medical tubing for use in liquid transfer and a medical solution bag device using the connector. More particularly, this invention relates to a connector for medical tubing used in transfusion of medicinal solution and blood or in dialysis of body fluids through the medium of tubes and a catheter, which permits two tubes or a tube and a catheter to be connected with perferct water tightness so that the tubes and the catheter so connected may provide a perfect barrier against invasion of microorganisms such as bacteria and viruses into the tubing through the portions of their connection and to a medical solution bag device, particularly transfusion bag means proper for peritoneal dialysis, using the connector.

2. Description of Prior Art

In the continuous therapy as by peritoneal dialysis, transfusion of medicinal solution or transfusion of blood, perfect protection of the tubing used in the therapy against invasion of microorganisms through the point of connection between two tubes or between a tube and a container or catheter constitutes a technical task.

In the therapy by dialysis, particularly peritoneal dialysis which is directed to the regions within the abdominal cavity which are totally destitute of defense against microorganic attacks, safe protection of the tubing used in the therapy against the microorganic invasion constitutes one absolutely essential technical task. The recent therapy by peritoneal dialysis is less complicate in mechanism and construction and notably less expensive than the conventional therapy by dialysis using an artificial kidney. The medical science has substantially elucidated the causes for periotoneal adhesion. Thus, the therapy of the latest development is capable of effectively precluding the peritoneal adhesion and lightening the burden on the patient to a great extent. Besides, a system for continuous ambulatory peritoneal dialysis which enables the patient to engage normally in his daily work and, at the same time, receive continued therapy has been invented and adapted perfectly for practical use. Thus, the therapy by peritoneal dialysis has come to reawaken and maintain deep interest. The reliability of the this particular method of dialysis regarding the safety of patient depends on the question as to whether or not the microorganic invasion of the tubing used in the dialysis can be perfectly prevented and, consequently, the plight of complicated peritonitis due to propagation of microorganisms within the peritoneum can be precluded. Unfortunately, it is held that the method of dialysis in its existing level is not capable of prolonged use.

The conventional method for continuous ambulatory peritoneal dialysis will be specifically described below. A catheter is surgically inserted into the abdominal cavity of a patient. A connector is attached to the external end of this catheter. With this connector, the other connector attached to the free end of a transfusion tube is coupled. Injection of a dialytic solution into the abdominal cavity is accomplished by hanging a bag containing the dialytic solution from a place higher than the abdominal cavity, piercing into the discharge port of the bag a bag syringe attached to the leading end of the transfusion tube, and loosening a clamp attached halfway along the length of the tube and fastened to stop up the passage within the tube. After the injection of the dialytic solution into the abdominal cavity is completed, the aforementioned clamp is tightened on the tube and the tube is properly rolled into a coil, and the bag is stowed neatly at the waist of the patient. Then, the patient is now free to walk around and engage in his normal work. After lapse of a stated length of time, the spent dialytic solution is withdrawn from the abdominal cavity. This withdrawal is effected by extending the tube, placing the bag on the floor, for example, and loosening the clamp on the tube. Then, the bag syringe is pulled out of the bag and the bag now containing the spent dialytic solution is discarded. The next dialysis is effected by setting a new bag containing fresh supply of dialytic solution at a high level and then piercing the bag syringe into the transfusion port of the new bag. This procedure is repeated for the third and following cycles of dialysis.

At present, whenever the connectors are coupled and the bag syringe is inserted into the discharge port of the bag in preparation for the first cycle of dialysis and each of the following cycles of dialysis, disinfecting works such as immersing the connectors momentarily in the solution of an iodine-based bactericide and thoroughly wiping the tip of the bag syringe with the bactericide are executed in order to prevent microorganic invasion of the tube interior. The bactericide in the solution enters the patient's body, though in a very small amount, and acts as a harmful substance. Thus, the bactericide is not allowed to be used in a high concentration but is required to be used in an extremely low concentration.

There has been also proposed equipment for continuous ambulatory peritoneal dialysis using a solution container connected by a flexible tube to a pateint's tube leading into the patient's abdominal cavity, which equipment comprises a flexible, foldable plastic container for dialytic solution provided with a transfer port extended therefrom, a flexible tube extended from the aforementioned transfer port and provided at the leading end thereof with a luer connector for connection to a luer connector attached to the patient's tube, and a breakable member provided in the aforementioned flexible tube and adapted to obstruct the flow of the solution within the tube until it is broken (Japanese Publication of Unexamined Patent Application No. 55-99257, corresponding to United Kingdom Patent Application GB Nos. 2,040,379A and 2,063,684A). This equipment also requires the leading ends of the tubes to be immersed in the bactericide or wiped thoroughly with the bactericide before it is put to use. By the same token, this equipment has a similar disadvantage.

The disinfecting works involved in the conventional devices, therefore, fall short of being justly called sterilization from the microorganic point of view. In fact, many cases of infection occurring through connectors and bag syringes on lapse of about two months' time after the start of dialysis and rounding up in complication with peritonitis have been reported. At present no effective measure is available for preventing this infection. Although the continuous ambulatory peritoneal dialysis proves to be a highly effective form of therapy as described above, it is held that this therapy cannot be safely performed for a long time.

OBJECTS OF THE INVENTION

It is, therefore, an object of this invention to provide a connector for a medical tubing used for liquid transfusion, which for the purpose of perfect disinfection before connection can be heated with a flame such as of an alcohol lamp without entailing undesired alternations such as rusting and surface deformation and which, therefore, can be repetitively connected and disconnected for a long period of time without any fear for invasion by bacteria and viruses and can be effectively used in the peritoneal dialysis directed to the regions within the abdominal cavity which are totally destitute of defense against microorganic attacks, and particularly effectively used in the system of continuous ambulatory peritoneal dialysis designed to be used for renewal of dialytic therapy by the patient himself at home at the place of his work without requiring the aid of a physician, and which also provides highly reliable protection of the tubing used in a wide range of therapeutic treatments including transfusion of medicinal solutions and transfusion of blood against invasion by microorganisms finding their way through points of connection.

Another object of this invention is to provide a medical solution bag which uses the connector mentioned above.

SUMMARY OF THE INVENTION

The objects described above are accomplished by a connector for a medical tubing used for liquid transfusion, which comprises a short tubular male connector member made of thermally resistant corrosionproof material, connected by insertion to the connecting end of one of the two flexible tubes subjected to mutual connection, and possessed of a male engaging portion having an insertion end shaped in a male form at the end thereof opposite from the aforementioned tube and further possessed of an inner passage; a short tubular female connector member made of thermally resistant corrosionproof material, connected by insertion to the connecting end of the other of the two flexible tubes subjected to mutual connection, and possessed of a female engaging portion having an insertion end shaped in the female form fit for fast insertion into the insertion end shaped in the male form of the aforementioned male connector member at the end opposite from the aforementioned tube and further possessed of an inner passage; and a fitting surface portion possessed by the aforementioned male connector member on the outer surface of the insertion end shaped in the male form being made of a material having a smaller thermal expansion coefficient than the material of a fitting surface portion possessed by the aforementioned female connector member on the inner surface of the insertion end shaped in the female form, and the fitting surface portion of the aforementioned insertion end shaped in the male form and the fitting surface portion of the aforementioned insertion end shaped in the female form possessed of relative sizes such as to permit the insertion ends to be connected to and separated from each other by shrink fit utilizing the difference between the thermal expansion coefficients.

Further, the objects described above are accomplished by a medical solution bag device, which comprises (A) a flexible bag proper of at least one solution transfer port, (B) a flexible tube connected to the aforementioned transfer port and adapted to guide the solution contained in the aforementioned bag proper during the discharge of the solution from the bag proper, (C) a tube to be connected to the aforementioned flexible tube, and (D) a connector for the aforementioned two tubes, which comprises a short tubular male connector member made of thermally resistant corrosionproof material, connected by insertion to the connecting end of one of the two tubes subjected to mutual connection, and possessed of a male engaging portion having an insertion end shaped in a male form the end thereof opposite from the aforementioned tube and further possessed of an inner passage; a short tubular female connector member made of thermally resistant corrosionproof material, connected by insertion to the connecting end of the other of the two flexible tubes subjected to mutual connection, and possessed of a female engaging portion having an insertion end shaped in the female form fit for fast insertion into the insertion end shaped in the male form of the aforementioned male connector member at the end opposite from the aforementioned tube and further possessed of an inner passage; and a fitting surface portion possessed by the aforementioned male connector member on the outer surface of the insertion end shaped in the male form being made of a material having a smaller thermal expansion coefficient than the material of a fitting surface portion possessed by the aforementioned female connector member on the inner surface of the insertion end shaped in the female form, and the fitting surface portion of the aforementioned insertion end shaped in the male form and the fitting surface portion of the aforementioned insertion end shaped in the female form possessed of relative sizes such as to permit the insertion ends to be connected to and separated from each other by shrink fit utilizing the difference between the thermal expansion coefficients.

As highly effective means for molding the fitting surface portions of the insertion ends of the aforementioned connector members in relative sizes capable of permitting the insertion ends to be connected to and separated from each other by shrink fit utilizing the difference between the thermal expansion coefficients, the present invention is described to be embodied so that the male connector member is made of ceramic material and the female connector member is made of a thermally resistant corrosionproof metal such as stainless steel, titanium, titanium alloy, nickel, nickel alloy, aluminum or chromium-plated brass or a thermally resistant corrosionproof plastic material such as polytetrafluoroethylene, polyimide, etc.

As effective means for enabling the fitting surfaces of the insertion ends of the two connector members to offer ample resistance to wear and permit ready generation of difference of sizes for shrink fit and, at the same time, allowing the fitting surfaces to be engaged with each other water tightly, this invention is desired to be embodied so that the fitting surfaces for mutual connection have matched tapered cylindrical surfaces.

As effective means for discouraging thermal degradation and thermal deformation and minimizing the number of work steps involved in the manufacture, this invention is desired to be embodied so that the connector member of the connector are joined to tubes made of silicone rubber throughout the entire length thereof.

As effective means for discouraging thermal degradation and thermal deformation and lowering the production cost, this invention is desired to be embodied so that the connector members of the connector are joined by insertion to tubes made of a flexible thermally nonresistant plastic material such as vinyl chloride resin, polyethylene or polypropylene through the medium of short tubular connecting tubes made of silicone resin (inclusive of silicone rubber) or ethylene tetrafluoride resin.

As means for establishing perfect, water-tight connection between the two connector members of the connector, the present invention is desired to be embodied so that the fitting surfaces of the insertion ends of the two connector members are each provided with at least one sealing member capable of water-tightly connecting the two connector members.

Further for the purpose of enabling the two connector members to be stably held in bare hands during their mutual connection or separation, this invention is desired to be embodied so that the tube side ends of the connector members are each covered with a tubular holder member made of a heat insulating material. Preferably in this embodiment, holder members made of silicone rubber are forcibly fitted on the outer surface of the end portions of the tubes and the tubes are tightly fastened on the connector members or holder members made of ethylene tetrafluoride resin, cork or glass fiber-reinforced resin are fitted not on the tubes but on the portions of the outer surfaces of the connector members closer to the tubes.

BRIEF DESCRIPTION OF THE DRAWINGS

FIG. 1 is a cross section illustrating the condition in which the connector according to this invention is held in a connected state, FIG. 2 is a cross section illustrating the condition in which the connector is held in a separated state, FIG. 3 and FIG. 4 are cross sections illustrating other embodiments of the connector of the present invention, FIGS. 5-7 are perspective views illustrating yet other embodiments of the connector of the present invention, FIG. 8 is a cross section illustrating a further embodiment of the connector of this invention as held in a connected state, FIG. 9 is a cross section illustrating still another embodiment of the connector of this invention as held in a separated state, FIG. 10 is a schematic diagram of a medical solution bag device according to the present invention, FIG. 11 is a cross section illustrating the mechanism of communication between a bag proper and a tube, FIG. 12 is a cross section illustrating the mechanism of communication in a tube.

PREFERRED EMBODIMENT OF THE INVENTION

Figure 13:
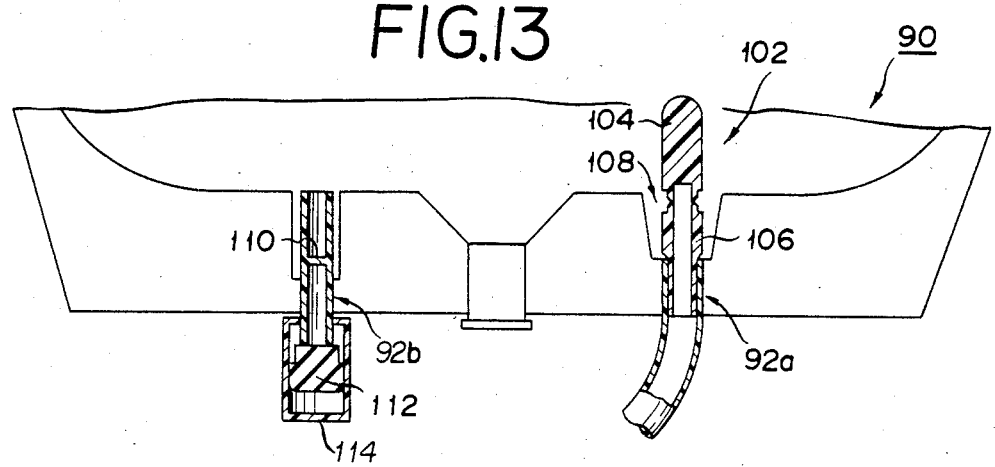
FIG. 13 is a cross section illustrating another embodiment of the mechanism for communication between the bag proper and the tube.

As illustrated in FIG. 1, the connector of this invention for medical tubing for liquid transfusion comprises a male connector member A connected to the connecting end of one tube $P_1$ of the two flexible tubes $P_1$ and $P_2$ used for medical liquid transfusion subjected to mutual connection and a female connector member B connected to the connecting end of the other tube $P_2$.

The male connector member A is made of ceramic such as zirconia, silicon nitride, alumina, steatite, forsterite, silica or silicon carbide. As illustrated in FIG. 2, it is provided with a flange 10 at a position falling halfway along the length of the outer surface thereof and with an insertion end 12 shaped in a male form in the portion thereof opposite the tube $P_1$ across the flange 10. The end of male connector member A adjoining the tube $P_1$ is a tube insertion end 16 shaped in the male form. The male connector member A has the shape of a short tube containing an inner passage 18. Externally the aforementioned insertion end 12 of the male form comprises a male tapered cylindrical surface 12a converging toward the free end thereof and a cylindrical outer surface 12b extending between the aforementioned male tapered cylindrical surface 12a and the aforementioned flange 10. The aforementioned female connector member B is made of a thermally resistant corrosion-proof plastic material such as stainless steel, titanium, titanium alloy, nickel, nickel alloy, aluminum, chromium-plated brass, polytetrafluoroethylene or polyimide. As illustrated in FIG. 2, the end of the female connector member B adjoining the tube $P_2$ forms a male tube insertion end 20 and the other end thereof forms an insertion end 22 of the female form capable of admitting into fast connection the insertion end of the male form of the aforementioned male connector member A. As a whole, the female connector member B has the shape of a short tube containing an inner passage 24 adapted to communicate with the aforementioned passage 18. The receding side of the aforementioned insertion end 22 forms a female tapered cylindrical surface 22a converging in the receding direction so as to admit into water tight connection the male tapered cylindrical surface 12a of the aforementioned male connector member A. The front end side of the insertion end 22 forms a cylindrical inner surface 22b of a diameter one size larger than the outer diameter of the cylindrical outer surface 12b of the aforementioned male connector member A so as to admit into fast connection the aforementioned cylindrical outer surface 12b. A thermally resistant corrosion-proof seal member 26 of the shape of an O ring is fitted in an annular groove formed about halfway along the length of the aforementioned cylindrical inner surface 22b. Optionally, annular retainers 14, 14 are tightly fitted around the tubes $P_1$, $P_2$ into which the insertion ends 16, 20 of the connector members are inserted.

The male connector member A and the female connector member B are so constructed that the possible leakage of the liquid through the point of connection between connector members is thoroughly precluded by the water-tight connection of the matched tapered cylindrical surfaces 12a and 22a of the male and female connector members A, B and the water tight connection of the seal member 26. As described above, the male tapered cylinderical surface 12a serves as the fitting surface of the insertion end 12 of the male form and the female tapered cylindrical surface 22a perfectly matching the male tapered cylindrical surface 12a serves as the fitting surface of the insertion end 22 of the female form. In other words, these two fitting surfaces have relative sizes such that they may be connected to and separated from each other by shrink fit utilizing the difference between the thermal expansion coefficients. The material of the male connector member A and that of the female connector member B are not necessarily limited to those respectively mentioned above. Insofar as the essential requirement that the two materials should both be thermally resistant and proof against corrosion and the material of the male connector member A has a smaller thermal expansion than that of the female connector member is satisfied, they may be a combination of two thermally resistant corrosionproof metal materials or a combination of a thermally resistant corrosion-proof metal material and a thermally resistant corrosionproof plastic material. To facilitate the shrink fit of the two fitting surfaces, the combination of a ceramic material and a metal material proves desirable from the standpoint of the contrast of thermal expansion coefficients. Particularly from the standpoint of the manufacture, it is desirable to form the female connector member B with a metal material and the male connector member A with a ceramic material. When the male connector member A is made of a ceramic material, among other materials mentioned above, the connector member derives from its extremely low thermal conductivity an advantage that it can be safely connected to the tube $P_1$ or $P_2$ which is made of an inexpensive, soft thermally nonresistant material such as vinyl chloride resin or polyethylene. When the female connector member B is made of a thermally resistant corrosion-proof metal material such as nickel plated brass, the tube $P_2$ to be connected thereto may be made of soft non-thermally resistant material as in the tube $P_1$, preferably silicone rubber resin or ethylene tetrafluoride resin in due consideration of the thermal conductivity of the metal material. Although the aforementioned seal member 26 is desired to be provided on the female connector member B, it may be provided on the male connector member A as occasion demands. When the seal member 26 is provided on the male connector member A, it is made of a material selected on condition that it should provide ample thermal resistance and corrosionproofness.

Optionally, the female connector member B is provided at the leading end thereof with a flange 28 corresponding to the flange 10 provided at the leading end of the aforementioned male connector member A. A thread is cut on the outer periphery of the flange 28. A tubular locking member 30 having a thread cut on the inner wall surface thereof is fixed on the male connector member A. The helical union of the inner thread of the tubular locking member 30 and the outer thread on the flange 28 locks the connector members A, B to each other.

FIG. 3 represents a modified embodiment aimed at obtaining a connector at a low production cost. The male connector member A is formed of an insertion tube 32 made of a ceramic material and possessed of a male tapered cylindrical surface 32a and a hand tube 34 made of a thermally resistant rigid plastic material and adapted to be helically connected to the aforementioned insertion tube 32. The female connector member B is formed of an insertion tube 36 possessed of a female tapered cylindrical surface 36a and made of a thermally resistant corrosionproof material such as stainless steel, titanium, titanium alloy, nickel, nickel alloy, aluminum or chromium-plated brass and a hand cylinder 38 adapted to be helically connected to the insertion tube 36 and made of a thermally resistant rigid plastic material. The insertion tube 36 is provided on the inner side thereof with a seal member 40. The hand tubes 34, 38 are connected to the tubes $P_1$ and $P_2$ made of a soft, thermally nonresistant material such as vinyl chloride resin, polyethylene or polypropylene.

Optionally if not essentially, the insertion cylinder 36 may be provided at the leading end thereof with a flange 42 having a thread cut on the periphery thereof. (Otherwise, the thread may be cut directly on the insertion tube 36.) The flange 44 on the insertion tube 32 is provided with a tubular locking member 46 having a thread cut on the inner wall surface thereof. The helical union of the outer thread on the flange 42 and the inner thread on the flange 44 locks the two connector members A, B to each other.

FIG. 4 represents a modified embodiment of the connector which accomplishes the connection of the male and female connector members by the union of perfectly matched inner and outer cylindrical surfaces in the longitudinal direction instead of the union of matched tapered inner and outer surfaces. The male connector member A is made of a ceramic material and is possessed of an insertion end 48 having a cylindrical outer surface 48a of one and the same diameter throughout the entire length thereof so as to fit the female connector member B. The female connector member B is made of a thermally resistant corrosionproof metal such as stainless steel, titanium, titanium alloy, nickel, nickel alloy aluminum or chromium-plate brass or a thermally resistant corrosionproof plastic material such as polytetrafluoroethylene, polyimide, etc. and possessed of an insertion end 50 having a cylindrical inner surface 50a of one and the same diameter throughout the entire length thereof so as to fit the male connector member A. The outside diameter of the cylindrical outer surface 48a is slightly larger than the inside diameter of the cylindrical inner surface 50a. When the cylindrical surfaces are heated, the difference between the outside diameter and the inside diameter mentioned above is reversed because of the difference of thermal expansion coefficients. The inside and outside diameters are such that the cylindrical surfaces are shrink fitted by utilizing the difference between the thermal expansion coefficients. The seal member 52 which is provided at the receding end of the cylindrical inner surface 50a is adapted so as to come into tight contact with the entire circumference of the insertion end face of the male connector member A to establish a water tight connection between the two connector members.

FIG. 5 represents a modified embodiment which pays due attention to the thermal resistance of the tubes to be connected to the male and female connector members where the two connector members are made of thermally resistant corrosionproof materials capable of withstanding the heat applied thereto in shrink fitting their fitting surfaces. The male connector member A and the female connector member B are fitted around short connection tubes 54, 56 each made of silicone resin or ethylene tetrafluoride resin. These connection tubes 54, 56 are connected to the tubes $P_1$, $P_2$ which are made of soft thermally nonresistant material such as vinyl chloride resin, polyethylene or polypropylene.

FIG. 6 represents a modified embodiment wherein the connector members are made of thermally resistant corrosionproof metal materials and adapted so as to be stably and conveniently held safely in bare hands while the connector is being disinfected by application of heat thereto.

The tubes $P_1$, $P_2$ which are made of silicone resin or ethylene tetrafluoride resin throughout the entire length thereof are fitted respectively around the male connector member A and the female connector member B. Around the outer surfaces of the portions of the tubes $P_1$, $P_2$ which are fitted around the male and female connector members A, B, tubular holder members 58, 60 made of silicone resin, cork, ethylene tetrafluoride or glass fiber-reinforced resin are forcibly fitted to keep the tubes $P_1$, $P_2$ down against the connector members.

FIG. 7 represents a modified embodiment which incorporates a holder member. The female connector member A is made of a ceramic material having a small thermal conduction and is directly connected, without requiring any holder member, to the tube $P_1$ which is made of a soft thermally nonresistant resin. The female connector member B is made of a thermally resistant corrosionproof metal material such as stainless steel, titanium, titanium alloy, nickel, nickel alloy, aluminum or chromium-plated brass. A tubular holder member 62 made of ethylene tetrafluoride resin or cork is directly fitted on the tube $P_2$ side of the female connector member B to an extent excluding the connection tube 64. The female connector member B is connected to the tube $P_2$ made of a soft thermally nonresistant resin through the medium of the connection tube 63 made of silicone resin or ethylene tetrafluoride resin.

FIGS. 8–9 represent another embodiment of the present invention. The male connector member A is made of a ceramic material such as zirconia, silicon nitride, alumina, steatite, forsterite, silica or silicon carbide. It is provided with a flange 66 at a position falling about halfway along the length of the outer surface thereof and an insertion end 68 of a male form at a position opposite the tube $P_1$ with reference to the aforementioned flange 66. The other end of the male connector member A for connection with the tube $P_1$ forms an insertion end 70 of a male form having a substantially uniform diameter toward the end face thereof. As a whole, the male connector member has the shape of a short tube containing an inner passage 72. The female connector member B is made of a thermally resistant corrosionproof metal such as stainless steel, titanium, titanium alloy, nickel, nickel alloy or chormium-plated brass or a thermally resistant corrosionproof plastic material. The end portion of the female connector member B for insertion with the tube $P_2$ forms an insertion end 74 of female form having a substantially uniform diameter toward the end face thereof. The other end portion thereof forms an insertion end 76 of female form capable of admitting into fast connection the insertion end 68 of the male form of the aforementioned male connector member A. As a whole, the female connector member is a short tube incorporating an inner passage 78 adapted to communicate with the aforementioned passage 72. On the inner surface of the insertion end 76 of the female connector member B, an annular groove 80 is formed and a thermally resistant corrosionproof seal member 81 of the shape of an O ring is fitted in this groove 80.

The fitting surface of the insertion end 68 of the male form and the fitting surface of the insertion end 76 of the female form have relative sizes such as to permit the insertion ends to be connected to and separated from each other by shrink fit utilizing the difference between the thermal expansion coefficients thereof. Optionally, the female connector member B may be provided at the leading end thereof with a flange 84 corresponding to a flange 66 provided at the leading end of the male connector member B. A thread is cut on the periphery of the flange 84. The male connector member A is provided thereon a tubular locking member 86 having a thread cut on the inner wall surface thereof. The helical union of the outer thread of the flange 84 and the inner thread on the tubular locking member 86 locks the two connector members A, B securely. The outer surfaces of the tubes $P_1$, $P_2$ into which the insertion ends 70, 74 are inserted are covered respectively with retainer members 75, 75 such as thermally shrinkable silicone tubes. The open end sides of the connector members A, B are kept covered each with a protective cap made of a thermoplastic resin such as vinyl chloride resin, ethylene-vinyl acetate copolymer, polyethylene or polypropylene for protection against microorganic invasion until they are put to use.

Now, concrete examples of the medical solution bag devices using the connectors of the aforementioned construction will be described below. As illustrated in FIG. 10, the medical solution bag device is generally provided with a bag proper 90. This bag proper 90 is made of a material which is flexible and generally capable of withstanding the harsh conditions of autoclave sterilization. Examples of the material are flexible vinyl chloride resin, crosslinked polyethylene-vinyl acetate copolymer, polypropylene, polycarbonate, polyamide, polyethylene terephthalate and polybutylene terephthalate. The bag proper 90 is provided with a solution transfer port 92a formed of a short tube and, as occasion demands, further with a solution mixing port 92b similarly formed of a short tube.

The solution transfer port 92a is provided with a connection tube 92 made of a flexible material and capable of withstanding the conditions of autoclave sterilization (such as the material mentioned above) and adapted to guide the solution (medicinal solution or blood) contained in the bag proper 90 during the discharge thereof from the bag proper 90. Optionally, the connection tube 92 is provided with a communication mechanism which keeps the connection tube 92 from communication with the solution in the bag proper 90 and prevents the solution from flowing out of the bag proper 90 until the solution is put to use and allows the connection tube 92 to communicate with the solution when the solution is put to use. This communication mechanism may be in any construction so far as it fulfills the function described above. For example, it may be formed of a pierceable dividing wall (not shown) formed in the solution transfer port 92a or the connection tube 92 and a hollow piercing member set in position within the solution transfer port 92a, so that the hollow piercing member is slid and pierced through the dividing wall to establish communication between the bag proper 90 and the connection tube 92 when the solution is put to use.

The communication mechanism illustrated in FIG. 11 comprises a hollow tube 94 having an outside diameter substantially equal to the inside diameter of the solution transfer port 92a and having the leading end thereof tapering and a solid cylinder 96 integrally formed at the leading end of the hollow tube 94. The solid cylinder 96 has an outside diameter smaller than the inside diameter of the solution transfer port 92a and larger than the inside diameter of the connection tube 92. The hollow tube 94 and the solid cylinder 96 are both made of a rigid plastic material such as, for example, rigid vinyl chloride resin and they are attached fast to the inner wall of the solution transfer port 92a. The connection tube 92 is inserted into and set fast to the solution transfer port 92a. An annular notch 98 is cut in the hollow tube 94 close to the boundary between the hollow tube 94 and the solid cylinder 96. The solid cylinder 96 blocks communication between the bag proper 90 and the connection tube 92 until the solution is put to use. To put the solution to use, the solid cylinder 96 is broken off the hollow cylinder 94 along the annular notch 98 by the pressure externally applied with the finger tips, for example, to establish communication between the bag proper 90 and the connection tube 92 via the interior of the hollow tube 94, with the result the solution contained in the bag proper 90 flows into the connection tube 92. On the end face of the solid cylinder 96, a protuberance 100 of the shape of a flat plate is formed throughout the entire outside diameter of the solid cylinder, so that the solid cylinder 96 broken off the hollow tube 94 may be prevented from clogging the entrance to the connection tube 92.

FIG. 12 shows that the communication means having the annular notch 98 and the hollow tube 94 is disposed along the way of the tube 92 between the solution transfer port 92 and the connector.

As illustrated in FIG. 10, the aforementioned connector members A, B to be finally connected to a catheter (not shown) are disposed at the farthest end of the connection tube 92. The aforementioned communication mechanism may be formed about halfway along the length of the connection tube 92 or at the end of the solution injection port 92 which is inserted into the bag proper 90.

FIG. 13 represents another embodiment of the medical solution bag device of this invention. This embodiment comprises a communication mechanism 102 serving to block the flow of the solution contained in the bag proper 90 until the solution is put to use and allow the flow of the solution when the solution is put to use and a solution mixing port 92b, both disposed independently of each other in the bag proper 90, with the communication mechanism 102 alone formed at the end of the solution transfer port 92a extended into the bag proper 90. The communication mechanism 102 comprises a tubular member 106 having an outside diameter substantially equal to the inner diameter of the solution transfer port 92a and provided at the leading end thereof with an integrally formed solid cylinder member 104, both made of a rigid plastic material such as, for example, a rigid vinyl chloride resin. An annular notch is formed around the boundary between the solid cylinder member 104 and the tubular member 106. The solid cylinder member 104 blocks the flow of the solution until the solution is put to use. At the time the solution is used, the solid cylinder member 104 is broken off the tubular member by being bent along the annular notch 108 under the pressure applied externally by finger tips, for example, to establish communication between the interior of the bag proper 90 and the connection tube 92.

The cavity in the solution mixing port 92b is blocked with a dividing wall 110. The solution mixing port 92b is provided at the external end thereof with a rubber member 112 encased with a cover 114. A medicine desired to be mixed with the solution inside the bag proper 90 can be introduced into the interior of the bag proper 90 by a syringe pierced through the cover 114, the rubber member 112, and the dividing wall 110 into the bag proper 90. After the syringe has been withdrawn, the rubber member 112 blocks the backflow of the solution.

The aforementioned connector members A, B are wholly sterilized and are immediately covered with protective caps (not shown) made of vinyl chloride resin or polypropylene so as to retain their sterilized state.

Figure 14:
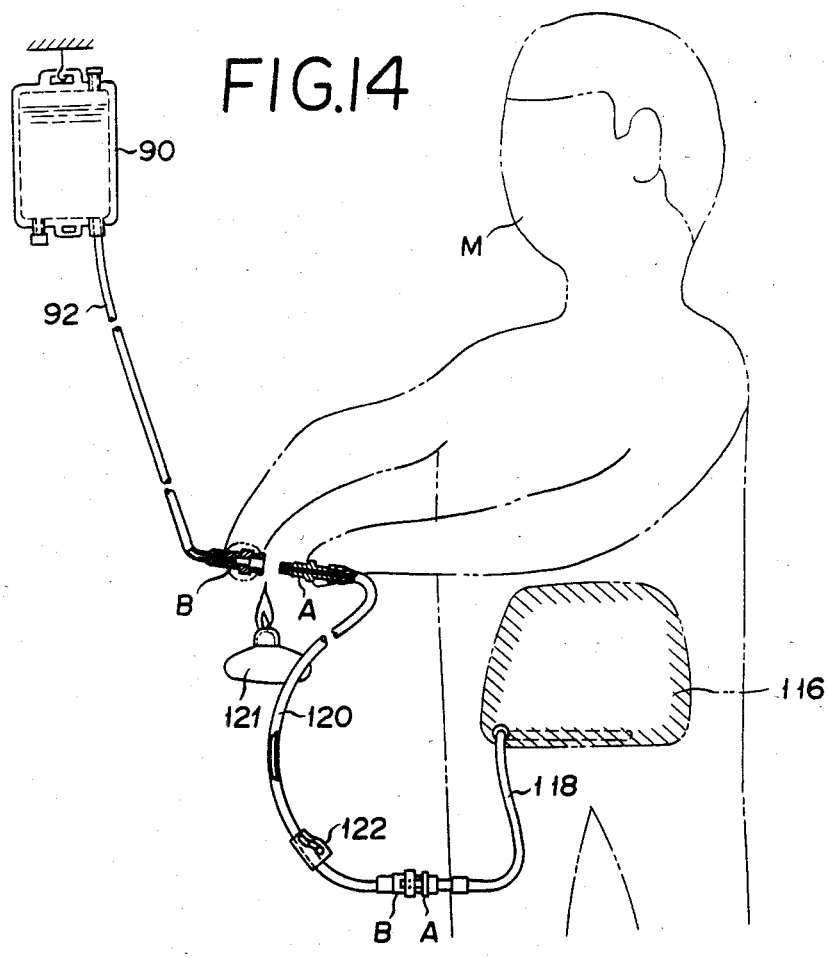
FIG. 14 is schematic diagram depicting a concept of the use of the medical solution bag means of this invention on a patient.

Now, a typical application of the connector and the medical solution bag device of the present invention to the continuous ambulatory peritoneal dialysis (CAPD) will be described. As illustrated in FIG. 14, a catheter 118 is surgically implanted in the abdominal cavity 116 of a patient M and the male connector member A is attached fast to the end of the catheter 118 outside the patient's body. Otherwise, the catheter 118 to which the male connector member A has been attached fast in advance is left to indwell within the abdominal cavity of the patient M. The patient picks up a tube 120 which has the connector members B, A joined to the opposite ends thereof as described above, removes the protective caps from the connector members, heats the exposed connector member B on the tube 120 and the connector member A on the catheter 118 with a flame such as of an alcohol lamp 121 to sterilize the connector members, and inserts the male connector member A into the female connector member B and leaves them to shrink fit to each other. Consequently, the two connector members are strongly coupled. Similarly, the patient sterilizes by the flame the female connector member B attached fast to the free end of the connection tube 92 connected to the solution injection port 92a of the bag proper 90 and the male connector A on the aforementioned tube 120 and connects them to each other by shrink fit. Subsequently, he hangs the bag proper 90 down from a high place, breaks the solid cylinder 96 or 104 in the communication mechanism by bending it along the annular notch 98 or 108 to establish communication between the bag proper 90 and the connection tube 92, and loosens the clamp 122 and allows the dialytic solution to flow down into the abdominal cavity. After the injection of the dialytic solution is completed, the patient tightens the clamp 122, rolls the tube 92 suitably into a coil, and fastens the bag proper 90 to his waist. Then, he is free to walk around or engage in his work. After elapse of a stated length of time, the dialytic solution is to be withdrawn from the abdominal cavity 116. This the patient accomplishes simply by unwinding the tube 92, placing the bag proper 90 on the floor, for example, and loosening the clamp 122 on the connection tube. Then, he separates the female connector member B on the connection tube 92 leading into the bag proper 90 from the male connector member A on the tube 120 while keeping the connector members sterilized with the flame and replaces the used bag proper 90 with a new supply. In this case the connector members A, B of catheter 118 side are still connected. The embodiment so far described represents a case wherein connectors are used at two points. In this case, when the intermediate tube 120 develops trouble of some form or other in the course of prolonged indwelling, it is discarded and replaced with a new supply. Of course by disconnecting the connector member A, B of the catheter 118 side, the connectors may be used at three or more points as occasion demands. Since the catheter 118 by nature is destined to indwell long, it is desired to be formed of a silicone tube, so that foreign matter will not readily adhere to the inner wall surface of the tube.

Now, the operation for the connection of the tubing will be described with reference to FIG. 14. Preparatorily to the first injection of the solution into the abdominal cavity, the indwelling catheter 118 is implanted within the abdominal cavity 118. The male connector member A at the external end of the catheter 118 and the female connector B at one end of the extension tube 120 are stripped of their protective caps. The exposed connector members are heated with the flame of an alcohol lamp, for example, and are fitted to each other. Then, the two connector members in the fitted state are pushed against each other and allowed to cool off spontaneously for a short time, with the result that they will be coupled with each other by shrink fit. Subsequently, the bag proper 90 is hung down from a stated height. The female connector member B at the leading end of the connection tube 92 and the male connector member A at the other end of the extension tube 120 are heated with the flame, fitted to each other, and left to cool off spontaneously in the same way as described above. Consequently, they are coupled with each other by shrink fit. The union of the two connector members by shrink fit is advantageously accomplished with ample strength because the fitting surface of the female connector member and the fitting surface of the male connector member are formed as matched tapered cylindrical surfaces and the former is made of a material having a larger thermal expansion than the latter and further because these surfaces are intensely heated prior to their mutual contact. Once the union is established, the two connector members will never be spontaneously separated. Their separation will barely occur when they are exposed to heat or to fairly large external force. Since the coupling occurs between the matched tapered cylindrical surfaces, the water tight fitting of the two connector members is completely effected with ample durability. The same effective union is obtained between the fitting surfaces of the connector members if the surfaces are not tapered cylindrical surfaces. When the connector is further provided with a locking mechanism, the fastness of the union between the connector members will be enhanced all the more by the locking mechanism. When the mutual coupling of the two connector members is completed, the blocking member 96 or 102 is broken off to establish communication between the bag proper 90 and the connection tube 92 and the clamp 122 on the extension tube 120 is loosened. Consequently, the solution contained in the bag proper 90 is gravitationally injected into the abdominal cavity 116. After the injection of the solution is completed, the clamp 122 is tightened on the extension tube 120 to block the inner passage of this tube 120. This completes the first cycle of the injection of the solution. Thereafter, the bag proper is wound on itself and the connection tube 92, the extension tube 120, and the catheter 118 are rolled into a coil and they are fastened to the patient's waist. Then, the patient is free to walkd around or engage in his work. To renew the dialysis for the second and subsequent cycles, the patient has only to remove the bag proper 90 from his waist, spread it flat on the floor, for example, and loosen the clamp 122 on the extension tube 120. Then, the spent dialytic solution within the abdominal cavity is gravitationally recovered in the bag proper 90. The bag proper 90, the connection tube 92, the blocking member 96 or 102, and the connector member B joined thereto are disposable. Preparatorily to their disposal, the clamp 122 is tightened and the portion of union between the male connector A and the female connector B is heated with the flame of an alcohol lamp to separte the two connector members from each other. Before this breakage of the union, the patient hangs a newly supplied bag proper 90 containing the solution from a high place and keeps near at hand the connector member joined to the leading end of the connection tube and still covered with a protective cap. Then, he heats the female connector B and the male connector member A to be separated with the flame of an alcohol lamp and, at the same time, applies separating force to the two connector members until they come off each other. The mutual separation of the two connector members is easily accomplished because the heat expands the female connector member more than the male connector member owing to the difference of their thermal expansion coefficients in much the same way as when the two members are coupled by the heating. When the female connector member B and the male connector member A are separated from each other as described above, the patient keeps the male connector member A heated in the flame and, at the same time, strips the female connector member B readied near at thand as described above, heats the exposed female connector member B in the same flame, then fits the sterilized male connector member A and female connector member B to each other, and allows them to cool off spontaneously until shrink fit. The mutual union of the two connector members and their separation both require application of heat. Since the separation and the union of the two connector members are carried out in or near the flame and, therefore, are accomplished sterilely, the possible leakage of microorganisms such as bacteria and viruses, the point of connection between the two connector members into the abdominal cavity can be completely prevented. Since the connector members are made of thermally resistant corrosionproof materials, they are not adversely affected by the heating with the flame. Thus, possible complication of peritonitis can be completely precluded. Of the pair of male and female connector members, it is desirable to use the latter at the end of the flexible tube connected to the bag proper and the former at the end of the connection tube. This is because the connector member on the connection tube nearer to the patient's body is destined to be used a multiplicity of times and further because the male connector member is sterilized more readily and completely with the flame than the female connector member.

As described above, the connector of this invention for the medical tubing for liquid transfusion comprises a pair of short male and female tubular connector members which are connected to the component tubes of a flexible therapeutic tubing and provided respectively with an insertion end shaped in a male form and an insertion end shaped in a female form. The male insertion end and the female insertion end are made of thermally resistant corrosionproof material, the fitting surface of the male insertion end is made of a material having a smaller thermal expansion than the fitting surface of the female insertion end, and the two fitting surfaces have sizes calculated to permit the two insertion ends to be connected to and separated from each other by shrink fit utilizing the difference between the thermal expansion coefficients.

With the connector of this invention for medical tubing for liquid transfusion, the coupling of the male insertion end and the female insertion end of the part of connector members is accomplished by heating the insertion ends with the flame, fitting the heated insertion ends to each other, then separating the mutually fitted insertion ends from the flame, and allowing them to cool off spontaneously. The separation of the coupled pair of connector members is accomplished by having the basal ends of the connector members held fast in hands, heating the point of their connection falling substantially halfway between the two hands with the flame, and applying mutually separating force to the connector members. Their union and separation are never attained unless the connector members are heated in the flame. The connector members will not undergo undesired alternations such as rusting and surface deformation when they are exposed to the heat. Thus, the possibility of the leakage of microorganisms such as bacteria and viruses through the point of connection is completely eliminated even when one pair of connector members are alternately connected and separated repetitively over a long period of time. Where an alcohol lamp or heater is available, the patient can safely and easily couple and separate the pair of connector members at home or at the place of his work without the aid of his physician and without the possibility of leakage of microorganisms through the point of connection.

When the connector of the present invention for the medical tubing is adopted for a liquid transfusion device being used for therapy, since the use of the flame as the source of heat ensures perfect sterilization of the connector members during their coupling and separation, the complication of peritonitis which tends to be induced by leakage of microorganisms into the abdominal cavity, the region totally defenceless to microorganic attacks, through the point of connection as during the peritoneal dialysis requiring a dialytic solution to be repeatedly injected into and withdrawn from the abdominal cavity, can be prevented. Thus, the long established practice of discontinuing the therapy by transfusion of medicinal solution, represented by the peritoneal dialysis, before it is continued so long as to suffer leakage of microorganisms through the point of connection into the abdominal cavity can be completely eliminated. Moreover, in accordance with the present invention, the operation of separation of coupled connector members and that of recoupling of separate connector members can be carried out by the patient all by himself. Thus, the connector of this invention proves to be ideal connecting means for the tubing used in the continuous mobile peritoneal dialysis.

Since the coupling of two connector members involved in the connector of this invention is effected by fitting their respective insertion ends to each other, the coupling can be obtained without imparting distortion to the tubes and the connector members can be smoothly coupled with each other. Moreover, the union of the insertion ends is effected by shrink fit and, therefore, is formed very powerfully. Also in this respect, the connector of this invention can be advantageously adopted for the continuous mobile peritoneal dialysis wherein the external force of tensile and compressive moments normally acts upon the connector members. The possibility of the union of the connector members being broken without being conceived by the patient himself will be substantially eliminated.

When the male connector member is made of a ceramics material and the female connector member is made of a thermally resistant corrosionproof metal material such as stainless steel, titanium, titanium alloy, nickel, nickel alloy, aluminum or chromium-plated brass or a thermally resistant corrosionproof plastic material such as polyfluoroethylene or polyimide as one aspect of the present invention, since the fitting surface of the insertion end of the male connector member is hardly expanded thermally, the fitting surface of the insertion end of the female connector member may be given an inside diameter slightly smaller than the outer diameter of the fitting surface of the insertion end of the male connector member, so that the fitting surfaces will have relative sizes such as to permit the respective insertion ends to be connected by shrink fit utilizing the difference between thermal expansion coefficients.

When the fitting surface of the connection end of the male connector member and that of the connection end of the female connector member are matched tapered cylindrical surfaces as one aspect of this invention, it is quite easy for the fitting surfaces of the two connector members to be fabricated so as to be coupled by shrink fit. At the same time, the two connector members can be joined water tightly and in shrink-fit union which promises high resistance to frictional wear.

When the excess lengths of the connector members are joined to tubes formed of silicone resin or rubber as one aspect of the present invention, the tubes are prevented from thermal degradation and thermal deformation and the number of work steps is decreased.

When the connector members are communicably connected to the tubes made of a nonrigid thermally nonresistant plastic material such as vinyl chloride resin, polyethylene or polypropylene each through the medium of a short tubular connection tube made of silicone rubber or ethylene tetrafluoride resin as one aspect of the present invention, although the connector as a whole additionally incorporates such connection tubes, the connection of connector members to the tubes can be effected more easily and the tubes can be produced inexpensively without raising the production cost of the connector. Consequently, the transfusion device can be offered at a lower cost.

When the fitting surfaces of the connection ends of the connector members are provided with seal members capable of water tightly connecting the connector members as one aspect of this invention, the connector members can be coupled with amply reliable, high water tightness.

When tubular holder members made of a heat insulating material are fitted around the tube side portions of the connector members as one aspect of the present invention, they permit the connector members to be held directly in bare hands even when they are made of metal materials. They also add much to the case with which the connector members are held in hands stably. And, they greatly facilitate the therapeutic operation which the patient himself is expected to perform. When this particular aspect of the present invention is modified by having holder members of silicone rubber forcibly fitted round the outer surfaces at the ends of the tubes thereby causing the tubes to be squeezed against the connector members, since silicone rubber is destitute of thermal shrinkage and thermal fusibility and rich in elasticity and tensile strength, the attachment of the connector members to the holder members is effected advantageously and, at the same time, the fitting of the tubes to the connector members is reinforced all the more. When holder members made of ethylene tetrafluoride, cork or glass fiber-reinforced resin are directly fastened with adhesive to the tube side portions of the connector members as one aspect of the present invention, the attachment of these holder members can be advantageously effected because the holder members lack elasticity and tensile strength.

What is claimed is:

1. A connector arrangement for medical tubing for liquid transfusion, the connector connecting together two flexible tubes, the connector arrangement comprising:

a tubular male connector member made of thermally resistant corrosionproof material, and having an end adapted to be connected by insertion to the connecting end of one of said two flexible tubes, said male connector member having a male engaging portion having a male insertion end shaped in a male form at the end thereof opposite from the aforementioned end connected to a tube, and further having an inner passage extending therethrough;

a tubular female connector member made of thermally resistant corrosionproof material, and having an end adapted to be connected by insertion to the connecting end of the other of said two flexible tubes, said female connector member having a female engaging portion having a female insertion end shaped in a female form which is dimensioned for fast insertion into the insertion end shaped in the male form of said male connector member at the end opposite from said other of said two tubes and further having an inner passage extending therethrough;

a first fitting surface portion provided on said male connector member on the outer surface of said male insertion end thereof; and a second fitting surface portion provided on an inner surface portion of said female insertion end of said female connector member;

said first fitting surface portion of said male connector member being made of a material having a smaller thermal expansion coefficient than the material of said second fitting surface portion of said female connector member, and said first fitting surface portion of said male connector member and said second fitting surface portion of said female connector member having relative sizes such as to permit the insertion ends thereof to be connected to and separated from each other by shrink fit utilizing a difference between the thermal expansion coefficients thereof;

wherein the materials forming said male and said female connector members including said first and said second fitting surface portions are capable of withstanding heating to a temperature sufficient for sterilization of both connector members, and said difference between the thermal expansion coefficients is selected to enable both connector members to be joined to and separated from one another at the sterilization temperature.

2. A connector according to claim 1, wherein said male connector member is made of a ceramic material and said female connector member is made of at least one of a thermally resistant corrosionproof metal material and a thermally resistant corrosionproof plastic material.

3. A connector according to claim 2, wherein said female connector member is made of a thermally resistant corrosionproof metal material.

4. A connector according to claim 3, wherein said thermally resistant corrosionproof metal material is selected from the group consisting of stainless steel, titanium, titanium alloy, nickel, nickel alloy, aluminum and chromium-plated brass.

5. A connector according to claim 1, wherein said first fitting surface of said male connector member and said second fitting surface of said female connector member are matched tapered cylindrical surfaces.

6. A connector according to claim 1, wherein fitting surface of said male connector member and said second fitting surface of said female connector member are matched parallelly cylindrical surfaces.

7. A connector according to claim 1, wherein at least one of said male and female connector members is provided with at least one seal member capable of liquid tightly connecting the connector members by sealing engagement with at least one of said male insertion end and said female insertion end.

8. A connector according to claim 7, wherein said seal member is an O ring.

9. A connector according to claim 1, which further comprises a locking mechanism coupled to said male and female connector members for locking said connector members together, thereby enhancing the union between said male and female connector members.

10. A connector according to claim 9, wherein said locking mechanism comprises a nut fitted around one of said connector members and a screw formed on the other of said connector members and adapted to be helically engaged with said nut.

11. A connector according to claim 1, further comprising two short tubes made of a thermally resistant corrosionproof plastic material, and wherein said male insertion end and said female insertion end are each connected to respective one of said short tubes made of a thermally resistant corrosionproof material.

12. A connector according to claim 1, wherein said flexible tubes are made of silicone resin or rubber.

13. A connector according to claim 1, wherein said connector members are provided at the mutually opposite ends thereof with short tubular connection tubes made of a thermally resistant flexible resin and said connection tubes are communicably connected to respective tubes made of a flexible thermally nonresistant plastic material.

14. A connector according to claim 1, further comprising hand tube members made of heat insulating material coupled coaxially to the tube insertion ends of said connector members.

15. A medical solution bag device, comprising:

a flexible bag containing a solution and having at least one solution transfer port, a first flexible tube connected to said transfer port and adapted to guide the solution contained in said bag during discharge of the solution from the bag, a second tube adapted to be connected to said first flexible tube, and a connector arrangement for coupling said first and second tubes together, said connector arrangement comprising:

a tubular male connector member made of thermally resistant corrosionproof material, and having a first end adapted to be connected by insertion to a connecting end of one of said first and second tubes, said male connector member having a male engaging portion having a male insertion end shaped in a male form at the end thereof opposite from the aforementioned first end thereof, and further having an inner passage extending therethrough;

a tubular female connector member made of thermally resistant corrosionproof material, and having a first end adapted to be connected by insertion to the connecting end of the other of said first and second tubes, said female connector member having a female engaging portion having a female insertion end shaped in a female form which is dimensioned for fast insertion into the insertion end shaped in the male form of said male connector member at the end opposite from said other of said first and second tubes and further having an inner passage extending therethrough;

a first fitting surface portion provided on said male connector member on the outer surface of said male insertion end thereof; and a second fitting surface portion provided on an inner surface portion of said female insertion end of said female connector member;

said first fitting surface portion of said male connector member being made of a material having a smaller thermal expansion coefficient than the material of said second fitting surface portion of said female connector member, and said first fitting surface portion of said male connector member and said second fitting surface portion of said female connector member having relative sizes such as to permit the insertion ends thereof to be connected to and separated from each other by shrink fit utilizing a difference between the thermal expansion coefficients thereof;

wherein the materials forming said male and said female connector members including said first and said second fitting surface portions are capable of withstanding heating to a temperature sufficient for sterilization of both connector members, and said difference between the thermal expansion coefficients is selected to enable both connector members to be joined to and separated from one another at the sterilization temperature.

16. A bag device according to claim 15, wherein said male connector member is made of a ceramic material and said female connector member is made of at least one of a thermally resistant corrosionproof metal and thermally resistant corrosionproof plastic material.

17. A bag device according to claim 16, wherein said female connector member is made of a thermally resistant corrosionproof metal.

18. A bag device accordig to claim 17 wherein said thermally resistant corrosionproof metal material is selected from the group consisting of stainless steel, titanium, titanium alloy, nickel, nickel alloy, aluminum and chromium-plated brass.

19. A bag device according to claim 15, wherein said first fitting surface of said male connector member and said second fitting surface of said female connector member are matched tapered cylindrical surfaces.

20. A bag device according to claim 15, wherein said first fitting surface of said male connector member and said second fitting surface of said female connector member are matched parallelly cylindrical surfaces.

21. A bag device according to claim 15, which further comprises communication means arranged in a path leading from the inner end of said solution transfer port inside said bag to said connector, said communication means including means for blocking the flow of the solution contained in said bag until said solution is to be put to use, and said communication means including means for opening said blocking means to allow the flow of the solution from said bag when said solution is put to use.

22. A bag device according to claim 21, wherein said communication means is disposed at the inner end of said solution transfer port within said bag.

23. A bag device according to claim 21, wherein said communication means is disposed in said solution transfer port.

24. A bag device according to claim 21, wherein said communication means is disposed in said first flexible tube between said solution transfer port and said connector.

25. A connector apparatus for medical tubing for liquid transfusion, the connector apparatus connecting together two flexible tubes, the connector apparatus comprising:

a tubular male connector member made of thermally resistant corrosionproof material, and having a first end adapted to be connected to one of said two flexible tubes, said male connector member having a second end opposite said first end thereof, said second end having a male engaging portion having a male insertion end shaped in a male form, said male connector member further having an inner passage extending therethrough;

a tubular female connector member made of thermally resistant corrosionproof material, and having a first end adapted to be connected to the other of said two flexible tubes, said female connector member having a second end opposite said first end thereof, said second end of said female connector member having a female engaging portion having a female insertion end shaped in a female form which is dimensioned for fast insertion into the insertion end shaped in the male form of said male connector member, said female connector member further having an inner passage extending therethrough;

a first fitting surface portion provided on said male connector member on the outer surface of said second end thereof;

a second fitting surface portion provided on an inner surface portion of said second end of said female connector member;

said first fitting surface portion of said male connector member being made of a material having a smaller thermal expansion coefficient than the material of said second fitting surface portion of said female connector member, and said first fitting surface portion of said male connector member and said second fitting surface portion of said female connector member having relative sizes such as to permit the insertion ends thereof to be connected to and separated from each other by shrink fit utilizing the difference between the thermal expansion coefficients thereof;

said male and female connector members having respective tubular connection tubes provided at said first ends thereof for connection to said flexible tubes, said connection tubes being made of a thermally resistant flexible resin; and communication means in communication with said inner passage of said male and female connector members and including blocking means for blocking the flow of a solution therethrough, said communication means including means for selectively opening said blocking means to permit flow of a solution through said inner passages of said male and female connector members.

26. A method for coupling and separating a connector arrangement for medical tubing for liquid transfusion under a sterilized state, using a connector for connecting together two flexible tubes, the method comprising:

coupling together a tubular male connector member and a tubular female connector member by heating them with a flame to sterilize said male and female connector members, inserting said male connector members into said female connector member, and allowing said male and female connectors to cool to shrink fit to each other to be strongly connected together; and then separating said coupled together male and female connector members by heating them with a flame to sterilize connector members, and then applying a separating force to said male and female connector members until they separate from each other;

the tubular male connector member being made of thermally resistant corrosionproof material, and having an end adapted to be connected by insertion to the connecting end of one of said two flexible tubes, said male connector member having a male engaging portion having a male insertion end shaped in a male form at the end thereof opposite from the aforementioned end connected to a tube, and further having an inner pasaage extending therethrough;

the tubular female connector member being made of thermally resistant corrosionproof material, and having an end adapted to be connected by insertion to the connecting end of the other of said two flexible tubes, said female connector member having a female engaging portion having a female insertion end shaped in a female form which is dimensioned for fast insertion into the insertion end shaped in the male form of said male connector member at the end opposite from said other of said two tubes and further having an inner passage extending therethrough;

a first fitting surface portion provided on said male connector member on the outer surface of said male insertion end thereof; and a second fitting surface portion provided on an inner surface portion of said female insertion end of said female connector member;

said first fitting surface portion of said male connector member being made of a material having a smaller thermal expansion coefficient than the material of said second fitting surface portion of said female connector member, and said first fitting surface portion of said male connector member and said second fitting surface portion of said female connector member having relative sizes such as to permit the insertion ends thereof to be connected to and separated from each other by shrink fit utilizing a difference between the thermal expansion coefficients thereof;

wherein the materials forming said male and said female connector members including said first and said second fitting surface portions are capable of withstanding heating to a temperature sufficient for sterilization of both connector member, and said dfference between the thermal expansion coefficients is selected to enable both connector members to be joined to and separated from one another at the sterilization temperature.

27. The method of claim 26, wherein at least one of said heating steps comprises placing said male and female connectors near said flame.

28. The method of claim 26, wherein at least one of said heating steps comprises placing said male and female connectors in said flame.

29. The method of claim 26, wherein said male connector member is made of a ceramic material and said female connector member is made of at least one of a thermally resistant corrosionproof metal material and a thermally resistant corrosionproof plastic material.

30. The method of claim 26, comprising providing said first fitting surface of said male connector member and said second fitting surface of said female connector member with matched tapered cylindrical surfaces.

31. The method of claim 26, comprising providing said first fitting surface of said male connector member and said second fitting surface of said female connector member with matched parallelly cylindrical surfaces.

32. The method of claim 26, comprising providing at least one of said male and female connector members with at least one seal member capable of liquid tightly connecting said connecting members together by sealing engaged members with at least one of said male insertion end and said female insertion end.

33. The method of claim 26, further comprising providing a locking mechanism coupled to said male and female connector members for locking said connector members together, thereby enhancing the connection between said male and female connector members.

34. The method of claim 26, comprising providing short tubular connection tubes at the mutually opposite ends of said connector members, said shorty tubular connection tubes being made of a thermally resistant flexible resin, and further comprising coupling said connection tubes to respective tubes made of a flexible thermally nonresistant plastic material.

35. The method of claim 25, comprising providing tubular holder members made of heat insulating material, and coupling said holder members to the tube side portions of said connector members such that said tube side portions are covered with respective tubular holder members.

* * * * *

UNITED STATES PATENT AND TRADEMARK OFFICE
CERTIFICATE OF CORRECTION

PATENT NO. : 4,588,402
DATED : May 13, 1986
INVENTOR(S) : A. IGARI et al

It is certified that error appears in the above-identified patent and that said Letters Patent is hereby corrected as shown below:

Column 1, line 41, "complicate" should read --complicated--;

Column 1, line 55, "after "of", insert --the--;

Column 4, line 12, after "form", insert --at--;

Column 13, line 50, "walkd" should read --walk--;

Column 14, line 16, "thand" should read --hand--;

Column 17, line 20 (claim 1), change "into" to --of--;

Column 18, line 3, (claim 6), after "wherein", insert --said first--;

Column 21, line 31 (claim 26), change "into" to --of--;

IN THE ABSTRACT: line 3, change "materia" to --material--.

Signed and Sealed this

Seventh Day of October, 1986

[SEAL]

Attest:

DONALD J. QUIGG

Attesting Officer     Commissioner of Patents and Trademarks